(12) United States Patent
Larreta-Garde et al.

(10) Patent No.: US 8,877,705 B2
(45) Date of Patent: Nov. 4, 2014

(54) BIOMATERIAL FOR THE CONTROLLED DELIVERY OF INGREDIENTS

(75) Inventors: Véronique Larreta-Garde, L'Isle Adam (FR); Julien Picard, Pontoise (FR); Marie Cécile Klak, Montmorency (FR); Sébastien Perrin, Maisons-Laffitte (FR); Sébastien Giraudier, Cergy (FR)

(73) Assignee: MA.I.A. Woundcare, Neuville sur Oise (FR)

( * ) Notice: Subject to any disclaimer, the term of this patent is extended or adjusted under 35 U.S.C. 154(b) by 831 days.

(21) Appl. No.: 12/742,588

(22) PCT Filed: Nov. 13, 2008

(86) PCT No.: PCT/FR2008/001596
§ 371 (c)(1),
(2), (4) Date: Sep. 1, 2010

(87) PCT Pub. No.: WO2009/095562
PCT Pub. Date: Aug. 6, 2009

(65) Prior Publication Data
US 2010/0330157 A1    Dec. 30, 2010

Related U.S. Application Data

(60) Provisional application No. 60/987,785, filed on Nov. 14, 2007.

(51) Int. Cl.
| | | |
|---|---|---|
| A61K 38/00 | (2006.01) | |
| A61K 31/715 | (2006.01) | |
| A61L 27/26 | (2006.01) | |
| A61K 47/36 | (2006.01) | |
| A61K 47/42 | (2006.01) | |
| A61L 27/54 | (2006.01) | |
| A61L 27/20 | (2006.01) | |
| A61K 9/06 | (2006.01) | |

(52) U.S. Cl.
CPC ............... *A61K 47/42* (2013.01); *A61L 27/26* (2013.01); *A61K 47/36* (2013.01); *A61L 27/54* (2013.01); *A61L 2300/602* (2013.01); *A61L 27/20* (2013.01); *A61K 9/06* (2013.01)
USPC .............................................. 514/1.1; 514/54

(58) Field of Classification Search
None
See application file for complete search history.

(56) References Cited

U.S. PATENT DOCUMENTS

| 2008/0317818 A1 | 12/2008 | Griffith et al. |
| 2009/0029411 A1 | 1/2009 | Larreta-Garde et al. |
| 2010/0330157 A1 * | 12/2010 | Laretta-Garde et al. ...... 424/450 |

FOREIGN PATENT DOCUMENTS

| WO | WO 2006/056700 | 6/2006 |
| WO | WO 2007/028258 | 3/2007 |

* cited by examiner

*Primary Examiner* — Michael Burkhart
(74) *Attorney, Agent, or Firm* — Harness, Dickey & Pierce, P.L.C.

(57) ABSTRACT

The disclosure relates to a biomaterial that comprises an aqueous phase, polymer network, a second polymer included in said disclosure invention more particularly relates to a biomaterial including an aqueous phase and a first polymer network made of a first proteic or saccharidic polymer or a mixture of first proteic and saccharidic polymers, wherein the first polymer network and the aqueous phase define a first gel (A), the biomaterial including: a second proteic or saccharidic polymer or a mixture of the second proteic and saccharidic polymers, either in solution in the aqueous phase of the gel (A) or in the form of a gel (B), and a first enzyme for degrading said second polymer or second polymer network. The disclosure also relates to a method for making biomaterials, and to the uses of the biomaterial particularly for releasing active substances, and to a device for the controlled release of active substances that include the biomaterial. The disclosure can particularly be used in the field of cosmetics and pharmaceuticals.

14 Claims, 5 Drawing Sheets

BIOMATERIAL FOR THE CONTROLLED DELIVERY OF INGREDIENTS

CROSS-REFERENCE TO RELATED APPLICATIONS

This application is a National Phase Entry of International Application No. PCT/FR2008/001596, filed on Nov. 13, 2008, which claims priority to U.S. Provisional Ser. No. 60/987,785, filed on Nov. 14, 2007, both of which are incorporated by reference herein.

TECHNICAL FIELD

The present invention relates to a biomaterial comprising an aqueous phase, a polymer network, a second polymer included in the network, and at least one enzyme for degrading the second polymer. The present invention also relates to a method for preparing said biomaterial. The present invention relates to uses of the biomaterial, in particular for releasing active substances, and to a device for the controlled release of active substances comprising the biomaterial. The biomaterial of the invention can in particular be used in the cosmetics and pharmaceutical fields.

BACKGROUND

Owing to their particular properties, gels are used in many fields, in particular the food section, the cosmetics field or the pharmaceutical field. A gel is composed of at least two components, one of which, which is very highly predominant, corresponds to a liquid solvent and the other of which is a component that can be described as solid. The two components are continuous throughout the entire medium. The "solid" phase constitutes a network which traps the "liquid" phase corresponding to the solvent, and prevents it from flowing. The medium as a whole behaves like a soft and elastic solid that is easy to deform.

Gels can be classified according to the type of links which form the network. Thus, two major gelling mechanisms can be distinguished, which result in "physical" gels or in "chemical" gels. Starting from a solution or from a dispersion in the liquid state, the formation of the gel is the result of the formation of a continuous solid network. This transformation is called solution/gel transition.

A physical gel is a supramolecular assembly constituted of molecules linked to one another by low-energy bonds (Van der Waals, hydrogen bonds, polar bonds, etc.). The stability of this assembly is associated with a precise range of physicochemical conditions (pH, concentration of molecules, temperature, solvent quality, ionic strength, etc.). Outside this range, the mixture is liquid. The sol/gel transition is therefore reversible for physical gels. Thus, a modification of the parameters of the medium can lead to the destruction of the structure and induce a gel/sol transition. Compositions for obtaining "physical" gels are well known from the prior art. Biogels are obtained essentially from macromolecules or polymers of natural origin: proteins or polysaccharides.

Gels described as "chemical" are also known in the prior art. A chemical gel corresponds to a supramolecular assembly, the molecules of which are associated by high-energy bonds (covalent bonds). The stability of this assembly is therefore very high. These chemical gels exhibit improved stability, the only means of performing a gel/solution transition consisting in destroying the covalent bonds of the network. For this reason, the sol/gel transition of chemical gels is said to be irreversible.

One family of chemical gels corresponds to enzymatically catalyzed gels. This gelling mode is especially observed in the major biological processes. Blood clotting, healing, skin formation and extracellular matrix assembly are biological processes where the change of soluble proteins into the gel state is essential. In vivo, a limited number of enzymes, for example lysyloxidases and transglutaminases, catalyze these reactions. In vitro, the most used is transglutaminase, which creates covalent bridges between the side chains of the lysine and glutamine residues of proteins.

Tgases thus catalyze the polymerization of proteins responsible for the formation of biological gelled networks. This family of proteins is ubiquitous and it is found both in prokaryotes and eukaryotes. Tgases make it possible to obtain gels from many proteins in the food industry, and in particular for manufacturing surimi or hardening many meat derivatives (ham, reconstituted food, etc.). By way of example of polymerizable proteins, mention may be made of gelatin, fibrin, gliadin, myosin, globulin (7S and 11 S), actin, myoglobin, whey proteins, in particular caseins and lactoglobulin, soy proteins, wheat proteins, and in particular glutenin, egg white and egg yolk, and in particular ovalbumin.

One of the protein gels most widely used is the gelatin gel. Gelatin is obtained from collagen, which is a structural protein. Collagen is a molecule that is organized into a triple helix. These triple helices can associate to form fibrils, which can associate to form fibers. The collagen triple helix is unstable at body temperature. Gelatin is obtained by denaturing collagen. The tissues containing collagen thus undergo an acid or alkaline treatment, which results in the denaturation of the collagen triple helix. The possibility of making fibers is then completely lost. An acid treatment results in formation of gelatin type A and an alkaline treatment results in a gelatin type B. The gelatin solution is therefore composed of isolated collagen chains. Since there are many uses for gelatin, it is sometimes necessary to create gelatin gels under conditions where physical gels do not exist (high temperatures, extreme pH or particular ionic strength). In order to form the network necessary for the gel, the gelatin chains are then bridged by covalent bonds, and in particular by the action of Tgases. The gels thus obtained are chemical gels. Greater control of the mechanical properties of the various chemical gels therefore constitutes essential stakes for extending their potentiality.

Analysis of the living world has revealed the existence of extremely dynamic systems. In living tissues, the cells are interacting with a structure called the extracellular matrix (ECM), which is rich in proteins and can be likened to a gel at the macroscopic level. This structure is mainly located under epithelial cells and around connective tissues. The cells can synthesize various extracellular matrix components, such as collagen, which confers its rigidity on the ECM, or fibronectin, which is involved in cell adhesion mechanisms. In parallel, the cell also produces proteases which generate extracellular matrix degradation. The cell is therefore simultaneously involved in the construction and degradation of the extracellular matrix. The structure of the extracellular matrix is not, therefore, an irreversible and static structure, but corresponds to a dynamic equilibrium resulting from the balance between the activities of construction and of degradation of the proteins synthesized by the cell.

Similarly, the clots formed according to the blood clotting mechanism also constitute dynamic systems. Thus, via a cascade of enzyme reactions, a clot is formed from soluble proteins which become organized in an insoluble network. This clot will then be eliminated during another enzyme reaction.

In these dynamic equilibria, the protein networks associate so as to become insoluble and form gels, which can be likened to solution/gel transitions. At the same time, the protein networks are also destroyed by the action of proteases, it being possible for this type of transition to this time be likened to gel/solution transitions. Successive transitions are thus sometimes witnessed, as in clotting, where the clot is first of all formed, and then degraded. Solution/gel transition in these biological processes is most commonly associated with the transglutaminase family mentioned above. The opposite transition, namely gel/solution, is associated with the antagonist activity of enzymes of the proteolytic type.

One of the most widely studied families is that of the matrix metalloproteinases (MMPs). They form a family of zinc-dependent endopeptidases which degrade most extracellular matrix proteins. However, a large number of different proteases exist. By way of example of families of proteases, mention may be made of serine proteases, such as trypsin or matriptase, cysteine and aspartate proteases, such as cathepsins B and L and cathepsins D and G, metalloproteases and the ADAM family. A large number of the enzymes orchestrating this type of reaction, such as transglutaminases or alternatively metalloproteases, have been characterized by biochemists and enzymologists.

Gels having the capacity for solution/gel and gel/solution transition are described in document WO 2006/056700. These gels comprise an aqueous phase, a polymer, and enzymes capable of degrading the polymer and of polymerizing monomers in order to form said polymer. In document WO 2006/056700, the "monomers" can be biological macromolecules or polymers. In addition, in this document, the term "polymer" applies to a "network of polymers".

The prior art gels exhibit programmed gelling and resolubilizing kinetics. Moreover, the prior art gels exhibit controlled physical characteristics, for example their viscoelasticity. Furthermore, the physical characteristics of the solid network and of the aqueous phase forming the prior art gels are indissociably and simultaneously modified. These drawbacks limit the field of application of these gels owing to their physical characteristics. It is, for example, impossible, according to the prior art, to modify the solid network without modifying the aqueous phase, or to modify the aqueous phase without modifying the solid network of gel.

There exists therefore a real need for novel biomaterials, in particular in the form of gels, of which the physical properties of just one of the two phases constituting the gel can be modified in a controlled manner. There also exists a need for novel gelled biomaterials capable of incorporating molecules, in particular active molecules (for example, cosmetic and/or pharmaceutical molecules), and of releasing these molecules in a controlled manner by modifying, in a controlled manner, the physical properties of just one of the two phases constituting the gelled biomaterial.

SUMMARY

The invention in fact makes it possible to meet these prior art needs and to overcome these drawbacks by providing a biomaterial in which the viscoelastic properties of the gel can be modified and in which the modification of these properties is programmed. A subject of the present invention is in particular a biomaterial comprising an aqueous phase and a first polymer network constituted of a first protein or saccharide polymer or of a mixture of first protein and/or saccharide polymers, in which the first polymer network and the aqueous phase form a first gel (A), the biomaterial comprising:

(i) a second protein or saccharide polymer or a mixture of second protein or saccharide polymers, the second polymer being different than the first polymer, and being included in the gel (A), either in solution in the aqueous phase of the gel (A), or in the form of a second polymer network constituting a gel (B), (ii) a first enzyme for degrading said second polymer.

According to the invention, the term "network" is intended to mean an association of molecules. This association between the molecules can be provided by strong or weak interactions (covalent bonds, hydrogen bonds, Van der Waals, etc.). In the case of covalent bonds, the association is a crosslinking and the network is said to be "crosslinked". The term "polymer" is intended to mean a macromolecule, for example a protein or saccharide polymer. A polymer network is an association of protein polymers or an association of saccharide polymers. The polymer network can constitute a gel.

According to the invention, the term "aqueous phase" is intended to mean an aqueous solution, for example water, for further example a buffered aqueous solution, for example buffered at a desired pH, for example by means of a phosphate or Tris buffer or any suitable buffer known to those skilled in the art as a buffer. It may, for example, be a medium which allows the activity of the enzyme(s) present in the biomaterial.

According to the invention, the first polymer network can be constituted of a first protein polymer. This first protein polymer can be chosen, for example, from the group comprising fibrin, gliadin, myosin, globulin (7S and 11S), actin, myoglobin, collagen and its derivatives, milk proteins, soy proteins, wheat proteins, egg-yolk and egg-white proteins, pea proteins, horse bean proteins, flax proteins, silk proteins, fibronectin, laminin, elastin and vitronectin, or a mixture of these polymers. This first polymer network can therefore be constituted of a single first protein polymer or of a mixture of first protein polymers.

According to the invention, the first polymer network can be constituted of a first saccharide polymer. This first saccharide polymer may be chosen, for example, from the group comprising carrageenans, alginates, xanthan, chitosan, chitin, hyaluronic acid, sulfated glycosaminoglycans, glycogen, cellulose and its derivatives, pectins, starch and its derivatives, dextrans and xylans, or a mixture thereof. This first polymer network can therefore be constituted of a single first saccharide polymer or of a mixture of first saccharide polymers.

According to the invention, the first polymer network can also be constituted of a mixture of first protein and saccharide polymers, chosen, for example, from the abovementioned groups of protein and saccharide polymers. According to the invention, the first polymer network can be chosen, for example, from the group comprising gelatin, fibrin and alginate gels, it being understood that this first polymer network is constituted of polymers that are different than the second polymers. According to the invention, the amount of the first polymer network or mixture of first polymers may be, for example, between 0.1% and 20% by weight, relative to the total weight of the biomaterial, preferably from 0.5% to 10% by weight.

According to the invention, the second polymer is different than the polymer constituting the first polymer network. This second polymer can be chosen, for example, from the group comprising fibrin, gliadin, myosin, globulin (7S and 11S), actin, myoglobin, collagen and its derivatives, milk proteins, soy proteins, wheat proteins, egg-yolk and egg-white proteins, pea proteins, horse bean proteins, flax proteins, silk proteins, fibronectin, laminin, elastin and vitronectin, or a mixture of these polymers. This second polymer may therefore be constituted of a single protein polymer or of a mixture of protein polymers. According to the invention, the second polymer can be chosen, for example, from the group comprising, for example, carrageenans, alginates, xanthan, chitosan, chitin, hyaluronic acid, sulfated glycosaminoglycans, glycogen, cellulose and its derivatives, pectins, starch and its derivatives, dextrans and xylans, or a mixture thereof. This second polymer can therefore be constituted of a single saccharide polymer or of a mixture of saccharide polymers.

According to the invention, the second polymer can also be constituted of a mixture of second protein polymers and second saccharide polymers, for example chosen from the abovementioned groups of protein and saccharide polymers. According to the invention, the second polymer can be chosen, for example, from the group comprising gelatin, fibrin, hyaluronic acid and alginate, it being understood that this second polymer is different than the first. According to the invention, the amount of the second polymer or mixture of second polymers can be between 0.01% and 20% by weight, relative to the total weight of the biomaterial, preferably from 0.1% to 10% by weight.

According to the invention, the first enzyme can be chosen, for example, from the group comprising enzymes of the metalloproteinase family, the serine protease family, the cysteine and aspartate protease family, the ADAM family, glycosidases, including amylase, cellulase, dextranase, pullulanase, pectinase, chitinase, xanthanase, chitosanase and hyaluronidase, and lyases, including hydroxyacetyl lyase, chondroitinase, heparinase and alginate lyase. According to the invention, the concentration of the first enzyme, in the biomaterial, can be between $2 \times 10^{-7}$ and 50 U/ml, preferably from $2 \times 10^{-6}$ to 20 U/ml.

According to the invention, the biomaterial may also comprise a second enzyme different than the first enzyme and capable of degrading the first polymer network, said first polymer network being capable of performing, under the action of said second enzyme, a gel (A)/solution transition. According to the invention, the second enzyme, different than the first enzyme, can be chosen, for example, from the group comprising enzymes of the metalloproteinase family, the serine protease family, the cysteine and aspartate protease family, the ADAM family, glycosidases, including amylase, cellulase, dextranase, pullulanase, pectinase, chitinase, xanthanase, chitosanase and hyaluronidase, and lyases, including hydroxyacetyl lyase, chondroitinase, heparinase, and alginate lyase. According to the invention, the concentration of the second enzyme, in the biomaterial, can be between $2 \times 10^{-7}$ and 50 U/ml, preferably from $2 \times 10^{-6}$ to 20 U/ml.

According to the invention, the biomaterial may also comprise a third enzyme different than the first and second enzymes and capable of generating bonds between said first polymers or mixture of first polymers, said third enzyme being capable of catalyzing a solution/gel (A) transition. According to the invention, the third enzyme can be chosen, for example, from the group comprising lysyloxidase, transglutaminases, disulfide isomerase proteins, sulfhydryl thiol oxidases, peroxidases, lipoxygenases, epimerases, including alginate epimerases, glucuronate isomerases, cellobiose epimerase and galactose-6-sulfurylases. According to the invention, the concentration of the third enzyme, in the biomaterial, can be between 0.01 and 50 U/ml, preferably from 0.1 to 5 U/ml.

According to the invention, the biomaterial may also comprise a fourth enzyme different than the first, second and third enzymes and capable of generating bonds between said second polymers or mixture of second polymers, said fourth enzyme being capable of catalyzing a solution/gel (B) transition. According to the invention, the fourth enzyme can be chosen, for example, from the group comprising lysyloxidase, transglutaminases, protein disulfide isomerases, sulfhydryl thiol oxidases, peroxidases, lipoxygenases, epimerases, including alginate epimerases, glucuronate isomerases, cellobiose epimerase and galactose-6-sulfurylases. According to the invention, the concentration of the fourth enzyme, in the biomaterial, can be between 0.01 and 50 U/ml, preferably from 0.1 to 5 U/ml.

According to the invention, the first, second, third and fourth enzymes are enzymes that may be, independently, active or may be activated. According to the invention, the aqueous phase of the biomaterial may also comprise an active substance. This active substance may, for example, be in solution in the aqueous phase of the gel (A) and/or in the gel (B).

According to the invention, the term "active substance" is intended to mean any substance or composition that has a biological or biochemical activity at the surface of an organism (microorganism or multicellular organism, for example skin, bone, organ, etc.) or in an organism. This active substance may, for example, have curative or preventive properties with regard to human or animal diseases. It may be any product that can be administered to humans or to animals, for the purpose of establishing a medical diagnosis or of restoring, correcting or modifying their organic functions. They may be bacteriostatic and/or bactericidal substances, antibiotics, disinfecting agents, colorants, etc.

According to the invention, the active substance can be chosen, for example, from the group comprising bacteriostatics, bactericides, vasodilators, dyes, including eosin, dextran blue, methylene blue, azure blue, proteins, saccharides, including hyaluronic acid and alginates, a liposome, a nanoparticle, a micelle, anti-acne agents, anti-allergic agents, anxiolytics, anti-asthmatics, anticancer agents, hypolipemic agents, hormonal contraceptives, antidepressants, antidiabetic agents, antalgics, antiasthenics, antihypertensives, antifungals, antibiotics, sleeping drugs, hormone treatments, antimigraine agents, drugs used to treat excess weight, antiparkinsonian agents, neuroleptics, nonsteroidal anti-inflammatories, ovulation inducers, mucolytics, antitussives, erection inducers and antiulceratives. According to the invention, it may be an active substance alone or a mixture of active substances.

According to the invention, the amount of active substance may depend, for example, on factors such as its activity and on the dose desired by the user. The desired dose can be readily determined by those skilled in the art, since this involves, for example, known doses for known products. According to the invention, the biomaterial of the present invention can therefore be used for the controlled release of at least one active substance.

The invention also relates to a method for preparing a biomaterial as described above, comprising the following steps:
a) formation, in the aqueous phase, of a first polymer network constituted of a first protein or saccharide polymer or of a mixture of first protein or saccharide polymers, the first protein or saccharide polymer or mixture of first protein or saccharide polymers forming said first polymer network,
b) addition of a second protein or saccharide polymer, or a mixture of second protein or saccharide polymers, different than the first polymer or than the mixture of first polymers, the addition step being carried out before the formation of the first polymer network.

According to the invention, the method of the invention can be carried out, for example, with second polymers or a mixture of second polymers included in the aqueous phase of the network of first polymers. According to the invention, the method of the invention can be carried out with second polymers or a mixture of second polymers forming, for example, a network of second polymers included in the network of first polymers. According to the invention, the formation or the degradation of the various polymers or polymer network can be induced by adding one to four enzymes in step b). The concentration of these various enzymes can make it possible, for example, to control the viscoelastic properties of the biomaterial of the invention.

According to the invention, the method of the invention can be carried out, for example, at a temperature of between 10 and 45° C. The first and second polymers are as defined above. The concentration of the first and/or of the second polymers can also be as described above.

According to the invention, the method may also comprise, in step b), the addition of a first enzyme capable of degrading said second polymers or the second polymer network. The first enzyme is defined above. The amount thereof is defined above.

According to the invention, the method may also comprise, in step b), the addition of a second enzyme capable of degrading the bonds of the first polymer network. The second enzyme is defined above. The amount thereof is defined above.

According to the invention, the method may also comprise, in step b), the addition of a third enzyme capable of generating bonds between said first polymers. The third enzyme is defined above. The amount thereof is defined above.

According to the invention, the method may also comprise, in step b), the addition of a fourth enzyme capable of generating bonds between said second polymers. The fourth enzyme is defined above. The amount thereof is defined above. According to the invention, the method may also comprise, in step b), the addition of at least one active substance. The active substance is defined above.

According to the invention, the method may also comprise a step c) in which the biomaterial is freeze-dried. According to the invention, it may also be a dehydration step. These steps make it possible to store the material of the present invention over long periods of time, and to subsequently rehydrate it for use.

The invention also relates to a device for the controlled release of an active substance comprising the biomaterial of the present invention. According to the invention, the releasing device may be chosen, for example, from the group comprising medical devices, including contact lenses, electrodes, sensors, care devices, dressings, impregnated compresses, bandages, surgical dressings, ophthalmic dressings, dental dressings, suture products, therapy devices, orthopedic articles, surgical implants, patches, transdermal gels, active patches, endoprostheses and implants for soft tissues, devices for tissue engineering, reconstruction materials, devices for cell culture, culture media, and culture supports.

The biomaterial of the present invention may, for example, partially or totally replace the material used in the abovementioned devices, in particular the material in contact with the skin, the mucous membranes, the organs, the bones, the cells, etc. In the cosmetics field, the biomaterial according to the invention may thus make it possible to prepare new cosmetics such as beauty masks or patches that can release a substance, for example, a substance which promotes the well-being of the user, or a cosmetic active agent, for example hyaluronic acid or retinol. In the pharmaceutical or cosmetics field, the biomaterial according to the invention can also make it possible to obtain gels that trap an active ingredient and are capable of releasing said active ingredient by returning to the solution state with given kinetics, for example gels or gelatin capsules that release the active ingredient after a given period of time. Other characteristics and advantages of the invention will emerge further on reading the description which follows, with reference to the attached figures.

BRIEF DESCRIPTION OF THE DRAWINGS

FIG. 6 A represents the effect of hyaluronic acid on the viscoelasticity (G': squares, G": triangles) of a physical gel containing collagenase (1.12×10$^{-4}$ U/ml) at a given frequency (6.3 rad·s$^{-1}$) as a function of time. 1% hyaluronic acid (black symbols) and gelatin alone (white symbols).

FIG. 6 B represents the change in viscoelastic properties (G': squares, G": triangles) of the physical gels, in the presence of hyaluronic acid (1%) and as a function of time, said gels containing various concentrations of collagenase: 0.95× 10$^{-4}$ U·ml$^{-1}$ (black symbols), 1.12×10$^{-4}$ U·ml$^{-1}$ (gray symbols), 1.29×10$^{-4}$ U/ml$^{-1}$ (white symbols).

FIG. 7 A represents the effect of hyaluronic acid on the viscoelasticity (G': squares, G": triangles) of a chemical gel containing collagenase (2.32×10$^{-4}$ U/ml) and transglutaminase (1.5 U/ml) at a given frequency (6.3 rad·s$^{-1}$) as a function of time. 1% hyaluronic acid (black symbols) and gelatin alone (white symbols).

FIG. 7 B represents the change in viscoelastic properties (G': squares, G": triangles) of the chemical gels, in the presence of hyaluronic acid (1%) and as a function of time, said gels containing transglutaminase (1.5 U/ml) and various concentrations of collagenase: 2.06×10$^{-4}$ U·ml$^{-1}$ (black symbols) 2.32×10$^{-4}$ U·ml$^{-1}$ (gray symbols), 2.58×10$^{-4}$ U/ml$^{-1}$ (white symbols).

EXAMPLES

Example 1

Method for Preparing a Biomaterial According to the Invention

A gelatin type A1 was used in this example. It is sold by the company Sigma (registered trademark) (G2500) and is derived from pig skin. The procedure for extracting it is an acid treatment, its pHi is equal to 8. Finally, it has a Bloom number of 300.

The hyaluronic acid used in this example is produced by the bacterium *Streptococcus equi* species. It was obtained by the company Fluka (registered trademark) (48178). It is a polysaccharide of about 1 million Daltons. The pKa of the gluruonic acid carboxyls is 2.4.

The alginate used in this example is extracted from the alga *Macrocystis pyrifera*. It is sold by the company Sigma (registered trademark) (A 2158). The fibrinogen used in this example is a fibrinogen type IV of bovine origin. It is sold by the company Sigma (registered trademark) (F 4753). It is 68% pure.

The transglutaminase (TG) used was produced by the company Ajinomoto under the name Activa WM (registered trademark). It is secreted by the bacterium *Streptoverticillium* sp. It molecular weight is 43 000 and it has an activity of 100 U.g$^{-1}$ at 40° C.

The collagenase used in the examples is a type IA zinc metalloprotease isolated from *Clostridium histolyticum* (Sigma, registered trademark, C-9891). Its molecular weight is 116 000. The maximum activity of enzyme is obtained in the presence of $CaCl_2$ and NaCl. It was shown that these elements interfere with the gelatin (results not provided); they were not used in the collagenase activity tests in the examples of the present application.

Thermolysin is a type X protease isolated from *Bacillus thermoproteolyticus* rokko (supplied by Sigma, P-1512). It is a zinc metalloprotease and its molecular weight is 34 600. Trypsin is a serine protease isolated from bovine pancreas. It is sold by Sigma (registered trademark), T-1426. Its MW is 23 800. Before being packaged by the preparer, the enzyme was treated with 2-1-tosylamido-2-phenylethyl chloromethyl ketone (TPCK) in order to reduce the chymotrypsin activity present with the trypsin.

The alginate lyase is extracted from *Flavobacterium* sp. It has an activity of 38730 U/g; it is sold by the company Sigma (registered trademark) (A 1603). The thrombin used is extracted from bovine plasma; it has an activity of 34.8 U/mg. It is sold by the company Sigma (T 4648).

A/ Method for Preparing a Biomaterial Comprising a First Polymer Network, a Second Polymer and a First Enzyme a) In this example, a biomaterial comprising a first polymer network which is a gelatin gel, the second polymer which is hyaluronic acid and a first enzyme which is hyaluronidase is produced.

For the preparation of the biomaterial, the samples were prepared with a concentration of 7% gelatin, 1% hyaluronic acid (weight-to-volume ratio) and various concentrations of hyaluronidase (1, 5 and 10 U/ml). The gelatin powder was incubated with 50 mM Tris-HCl buffer at pH 7.4 and stored at 4° C. for 15 minutes. The hyaluronic acid was then deposited at the surface of the solution. The preparation was then solubilized with stirring at 40° C., at most for 15 minutes. A solution of hyaluronidase, previously prepared in the same buffer at an initial concentration at least five times higher than the final concentration, is mixed with the preparation of gelatin and hyaluronic acid. In order to obtain a physical gel, a temperature ramp of 40° C. to 27° C. was applied to the solution, with a decrease in temperature of 0.5° C. per minute.

b) In this example, a biomaterial comprising a first polymer network which is a gelatin gel, the second polymer which is alginate and a first enzyme is alginate lyase is produced.

The biomaterial is made up of 5% gelatin, 1% alginate and 0.2 U/ml of alginate lyase. In order to obtain this gel, a solution of 50 mM Tris-HCl buffer at pH 7.4 is added to gelatin powder. An alginate solution is prepared beforehand (in the same buffer) and added to the gelatin. The mixture is incubated for 30 minutes at 40° C. A solution of alginate lyase is then added to the reaction medium and the mixture is incubated at 27° C.

c) In this example, a biomaterial comprising a first polymer network which is an alginate gel, the second polymer which is gelatin and a first enzyme which is either collagenase or trypsin or thermolysin is produced.

The biomaterial is made up of 1% alginate, 1% gelatin and a protease. The sodium alginate (0.1 g) is dissolved in a freshly prepared solution of calcium-EDTA (282 mg $CaCl_2.2H_2O$ and 798 mg $Na_4EDTA.2H_2O$ in 10 ml) without heating. A 5% gelatin solution is prepared in water, and the mixture is stored at 4° C. for at least 4 hours before use. The solutions are mixed so as to obtain final concentrations of 1% alginate and 1% gelatin, and the mixture is incubated at 40° C. for 30 min. A 3 M solution of D-glucono-6-lactone is prepared extemporaneously and 312 µl thereof are added to the previous mixture at the same time as the protease. The final concentration of collagenase is $1.12 \times 10^{-5}$ U/ml. The final concentration of thermolysin is $3.25 \times 10^{-4}$ U/ml. The final concentration of trypsin is $2.46 \times 10^{-4}$ U/ml. The mixture is incubated at 40° C. and the gelatin is then in the form of a solution. If the mixture is incubated at a temperature of 25° C. or 10° C., the gelatin is in the form of a gel.

B/ Method for Preparing a Biomaterial Comprising a First Polymer Network, a Second Polymer, a First Enzyme and a Second Enzyme In this example, a biomaterial comprising a first polymer network which is a gelatin gel, the second polymer which is hyaluronic acid, a first enzyme which is hyaluronidase and a second enzyme which is either collagenase or trypsin or thermolysin is produced. The biomaterials are prepared with the same experimental protocol as the biomaterial prepared in A-a), and protease (either collagenase or trypsin or thermolysin) is added to the gelatin solution. The volume of the enzyme samples corresponds at least to 20% of the final volume, in order to optimize the distribution in the gelatin solution. A single solution containing the first and the second enzyme is prepared in a water bath with electromagnetic stirring at 40° C., before being added to the gelatin. The final concentration of collagenase is $1.12 \times 10^{-4}$ U/ml. The final concentration of thermolysin is $3.25 \times 10^{-3}$ U/ml. The final concentration of trypsin is $2.46 \times 10^{-3}$ U/ml.

C/ Method for Preparing a Biomaterial According to the Invention, Comprising a First Polymer Network, a Second Polymer, a First Enzyme and a Third Enzyme a) In this example, a biomaterial comprising a first polymer network which is a gelatin gel, the second polymer which is hyaluronic acid, a first enzyme which is hyaluronidase, and a third enzyme which is transglutaminase, is produced.

For the preparation of the biomaterial, the samples were prepared with a concentration of 7% gelatin, 1% hyaluronic acid (weight-to-volume ratio), 1.5 U/ml of transglutaminase and various concentrations of hyaluronidase (1.5 and 10 U/ml). The gelatin powder was incubated with 50 mM Tris-HCl buffer at pH 7.4, and stored at 4° C. for 15 minutes. The hyaluronic acid is then deposited at the surface of the solution. The preparation was then solubilized with stirring at 40° C., at most, for 15 minutes. A solution of hyaluronidase and transglutaminase, prepared beforehand in the same buffer at an initial concentration at least five times higher than the final concentration, is mixed with the preparation of gelatin and hyaluronic acid.

b) In this example, a biomaterial comprising a first polymer network which is a fibrin gel, the second polymer which is hyaluronic acid, a first enzyme which is hyaluronidase, and a third enzyme which is thrombin, is produced.

The biomaterial contains 4.8 mg/ml of fibrinogen, 0.24 mg/ml of hyaluronic acid, 0.2 U/ml of thrombin, 1 U/ml of hyaluronidase, $2 \times 10^{-2}$ mol/l of $CaCl_2$ and $15 \times 10^{-2}$ mol/l of NaCl. All the constituents are dissolved in 50 mmol/l Tris-HCl buffer at pH 7.4, preheated to 37° C. The fibrinogen is mixed beforehand with the $CaCl_2$, with NaCl and with the hyaluronic acid. The solution of thrombin and hyaluronidase is then added to the reaction medium, and the mixture is incubated at 37° C.

D/ Method for Producing a Biomaterial Comprising a First Polymer Network, a Second Polymer, and a First, a Second and a Third Enzyme In this example, a biomaterial comprising a first polymer network which is a gelatin gel, the second polymer which is hyaluronic acid and a first enzyme which is hyaluronidase, a second enzyme which is either collagenase or trypsin or thermolysin and a third enzyme which is transglutaminase is produced. This biomaterial is prepared like C-a), but this time, a protease (either collagenase or trypsin or thermolysin) is added to the enzyme mixture of transglutaminase and hyaluronidase. The final concentration of collagenase is $2.32 \times 10^{-4}$ U/ml. The final concentration of thermolysin is $6.5 \times 10^{-3}$ U/ml. The final concentration of trypsin is $4.35 \times 10^{-3}$ U/ml.

Example 2

Eosin Release by Gels

In this example, the first polymer network is a gelatin gel, with or without the second enzyme which is collagenase and the third enzyme which is transglutaminase. For the preparation of the biomaterial, the samples were prepared with a concentration of 5% gelatin, 1 U/ml of transglutaminase, 0.1 mg/ml of eosin (Sigma) and, optionally, $3.5 \times 10^{-5}$ U/ml of collagenase. The gelatin powder was incubated with 50 mM Tris-HCl buffer at pH 7.4, containing the eosin, and stored at 4° C. for 15 minutes. It was then solubilized with stirring at 40° C., at most, for 15 minutes. A solution of transglutaminase and, optionally, collagenase, prepared beforehand in the same buffer, at an initial concentration at least five times higher than the final concentration, is mixed with the gelatin preparation.

The purpose of this example is to show that the gels which do not comprise any second polymer do not allow the controlled release of a low-molecular-weight substance. The gel containing the collagenase was formed in thirty minutes, and became liquid again (solubilization time) in about twenty hours.

Figure 1:
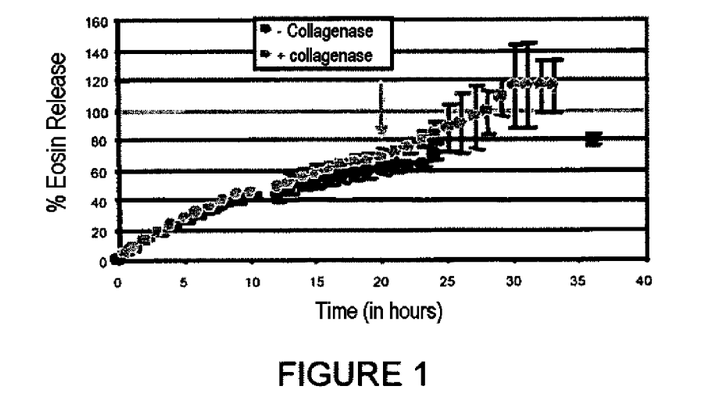
FIG. 1 represents the change in eosin release over time in a biomaterial according to the invention; the arrow represents the resolubilization time for the gel comprising collagenase.

A second gel was also formed. This second gel was composed of 5% gelatin and 1 U/ml of transglutaminase. The eosin release was monitored over time by spectrophotometry at 517 nm; the increase in the signal correlates directly with the eosin release. The eosin release by the gel is continuous (FIG. 1) in the presence or absence of collagenase in the gel.

Example 3

Dextran Blue Release by a Gel

Figure 2:
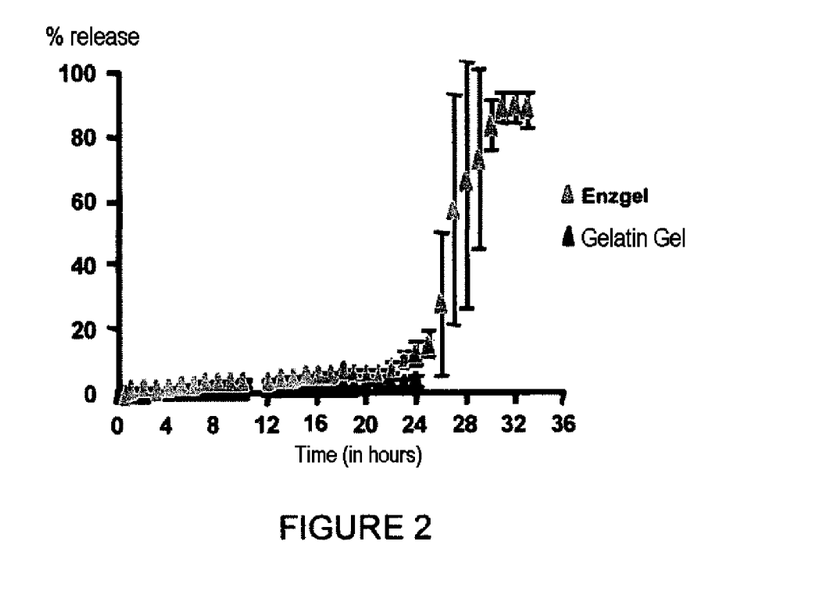
FIG. 2 represents the percentage release of dextran blue as a function of time in a biomaterial according to the invention.

The biomaterials used in this example are identical to those used in Example 2, except that the eosin was replaced with dextran blue (MW 2 000 000) at a final concentration of 5 mg/ml. The dextran blue release was monitored by spectrophotometry at 620 nm; the increase in the signal correlates directly with the dextran blue release. No dextran blue release was observed as long as the gel is in gel form (FIG. 2). The release of the colorant was observed during the solubilization of the gel, i.e. 24 hours after gelling.

The release of molecules present in gels depends on the viscoelastic properties of the gel. In this case, the release of active substance is solely linked to the gel resolubilization time. The release of active substance during the gel phase is not therefore controlled.

Example 4

Method for Studying the Elasticity and the Viscosity of the Biomaterial

The study of the elasticity and of the viscosity of the gels was carried out by studying the rheological parameters of the gel. The definition of rheology was established in 1929 by the American Society of Rheology. It comprises all studies on the flows and deformations of materials. It principle consists in applying a stress (elongation, compression, shear, etc.) to a sample, and results in the deformation thereof. The relationship between the stress and the deformation depends on the intrinsic properties of the sample and on the external conditions. The deformation used in rheology studies is the shear movement. A particularly simple example of shear concerns the movement of a sample between two flat surfaces, one of which is immobile and the other of which can move parallel to itself.

Under the effect of the shear, the flat layers of the sample flow parallel to one another, with different velocities. The layer in contact with the mobile surface moves with it at the same speed, whereas that in contact with the immobile surface does not move; this is what is referred to as the no wall slip hypothesis. From there, a layer movement velocity gradient becomes established and two quantities characterize the shear:

The shear velocity which corresponds to the variation in velocity between the limiting layers. It is expressed as the inverse of a time $(s^{-1})$.

The shear strength τ which is relative to the tangential friction forces between the various layers. The unit thereof is the Pascal (Pa).

Oscillatory or dynamic analysis consists in imposing a shear movement which oscillates with a given pulsing, ω. In this case, the stress (τ) and the deformation (γ) change in a sinusoidal manner over time, with the same pulsing but with a certain phase shift. Several quantities are characteristic:

The phase shift δ between the deformation and the stress.
The ratio $G^*=(\tau_0)/(\gamma_0)$, where $\tau_0$ and $\gamma_0$ represent, respectively, the stress and the deformation of maximum amplitude.

This ratio is called the shear modulus. It is a complex number made up of an elastic component (the storage modulus) and a viscous component (the loss modulus). The moduli have the dimension of a stress with a unit in Pascal (Pa).

$$G^*_{(\omega)}=G'_{(\omega)}+iG''_{(\omega)}$$

The phase shift δ is connected to these two components by:

$$G'=G^*\cos\delta$$

$$G''=G^*\sin\delta$$

As a result:

$$\tan\delta=G''/G'$$

For a purely viscous system, the phase shift between the stress and the deformation is equal to 90°, thus the value of G'=0, and G" is determined as the viscous modulus. On the other hand, for an elastic solid, it is G" which is equal to 0. The storage modulus is also called elastic modulus. It is clear that, if δ is between 0 and 45°, the material has a more elastic than viscous behavior, whereas the opposite is true if 6 is between 45 and 90°.

The gelling processes are characterized by a gel point, which corresponds to the fraction of created bonds that is necessary for the formation of the gel. The gel time is itself determined by means of the time that is necessary to reach the gel point. In rheology, the gel time can be considered to be the time necessary for the angle of phase shift δ, between a stress and an oscillating deformation, to reach a value of 45° and therefore for the G"/G' ratio to be equal to 1. In this case:

When G">G', and tan δ>1, it can be considered that the sample is liquid.
When G'>G", and tan δ<1, the sample is gelled.
When G'=G" and tan δ=1, the sample is at the gel point.

This definition of the gel point takes into consideration the fact that the relaxation times are infinite in the linear range of the gel and therefore that the viscoelastic parameters are independent of the measuring conditions.

Another way to consider the gel point is verification, by means of a rheometer, of the oscillatory deformation. In the examples below, the rheometer used is a RheoStress 150 from ThermoElectron (registered trademark). The system of the rheometer is a cone/plate system, with an applied deformation (an applied stress is possible). The real deformation was verified using an iterative method which consists in applying a torque (a stress) and in recording the resulting deformation until the correct deformation is obtained.

Two cones were used for the experiments. They are both made of titanium and have an angle of 2°. On the other hand, they differ in terms of their diameter, which is 35 mm for one and 60 mm for the other.

The rheometer was connected to a cryostat F6 (ThermoElectron) which makes it possible to thermostat the support on which the sample lies. In order to prevent evaporation, a system which creates a humid chamber is used. In addition, silicone oil (50 mPa·s) was added to the channel of the support for maximum prevention of exchanges between the samples and the air. The rheometer was controlled by a computer and Rheowin (registered trademark) software.

Example 5

Study of the Effect of the Degradation of the Second Polymer on the Polymer Network The purpose of this example is to demonstrate the effect of the degradation of the second polymer, by the first enzyme, on the biomaterial of the invention. In this example, the preparation of the gels was carried out according to the methods described in Example 1 A-a). The compounds used in this example are identical to those given in Example 1 A-a).

The various measurements of elasticity of the biomaterial were carried out with the rheometer given in Example 4. In the examples, the elasticity of the biomaterial, or elastic modulus, was measured according to the method given in Example 4.

In the examples, the viscosity of the biomaterial was measured with the method given in Example 4.

In this example, the biomaterial tested comprises:
 as first polymer: gelatin, and therefore as first polymer network: a gelatin gel (gel (A)),
 as second polymer: hyaluronic acid, and
 as first enzyme: hyaluronidase.

In this example, various concentrations of hyaluronidase were added to a solution of gelatin at 7% and hyaluronic acid at 1%. A temperature ramp of 40° C. to 27° C. was then applied for gelling. The hyaluronidase concentrations used are 1, 5 and 10 U/ml. This concentration range made it possible to evaluate the possible effect of the degradation of the hyaluronic acid on the gelling, but also to quantify these effects.

Figure 3:
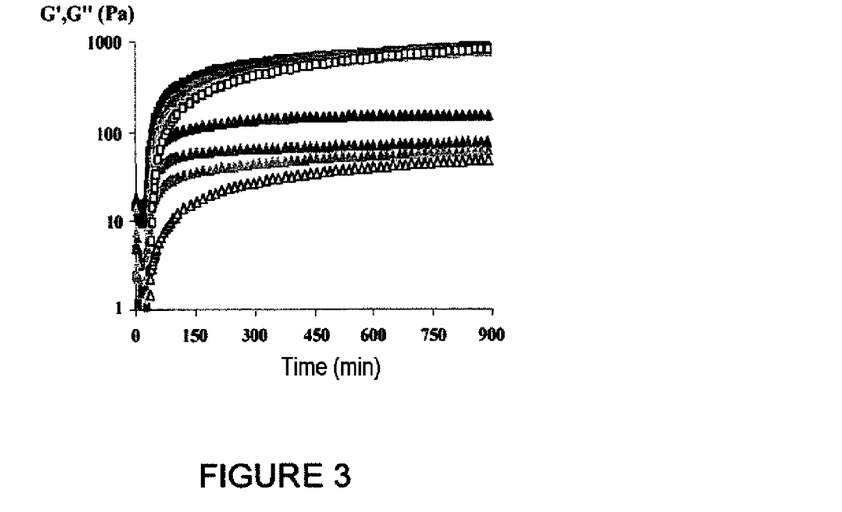
FIG. 3 represents the influence of the degradation of hyaluronic acid (1%) on the viscoelasticity (G': squares, G": triangles) of the physical gel at a given frequency (6.3 rad·s$^{-1}$) as a function of time in minutes. 1 U/ml of hyaluronidase (black symbols), 5 U/ml of hyaluronidase (dark gray symbols), 10 U/ml of hyaluronidase (light gray symbols) and gelatin alone (white symbols).

For all the gels containing hyaluronidase, the elasticity appears to converge, after 900 minutes, toward a G' having a value equivalent to that of the gelatin physical gel alone. At the same time, it is noted that the viscosity (G") decreases as a function of the hyaluronidase concentration (FIG. 3). This result therefore shows that hyaluronic acid degradation can take place in the gelled medium. No effect of the oligomers, produced from degradation of the hyaluronic acid, was observed on the gelling of the physical gel (results not provided).

In order to show that the degradation of the second polymer does not act on the polymer network, the biomaterial was observed by polarimetry. A solution containing 1% hyaluronic acid, 7% gelatin and 1 U/ml of hyaluronidase was gelled according to the method described in Example 1. The formation of triple helices, over time, was monitored by polarimetry and compared with that of the same solution in the absence of enzyme.

The polarimeter used is a Jasco 1100 (registered trademark), equipped with a Julabo F 25 external cryostat, the temperature being computer-managed. It measures the angle with an accuracy of 0.001°. The glass cell has an optical path of 0.1 dm and a volume of 1 ml. The cuvette can be thermostated, by means of a water-circulation jacket connected to the cryostat. The temperature, thus regulated, was measured directly in the cuvette by means of a probe connected to the polarimeter. All the measurements of the study were carried out at 436 nm.

A computer was connected to the polarimeter and software records the angle and the temperature in the cuvette as a function of time. The software of the Jasco is the "Spectra Manager" (registered trademark), whereas the cryostat is managed using the "Julabo EasyTemp" software (registered trademark).

Figure 4:
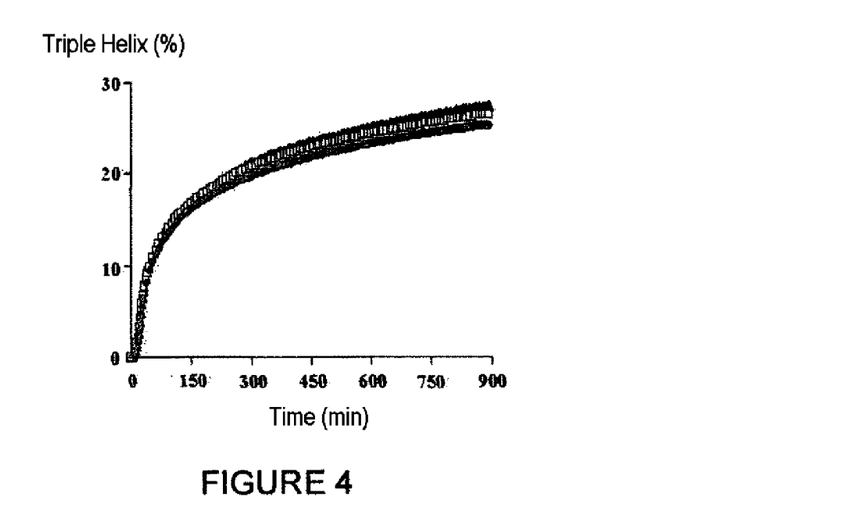
FIG. 4 represents the influence of the degradation of hyaluronic acid (1%) on the formation of triple helices of the physical gel as a function of time in minutes. 1 U/ml of hyaluronidase (white symbols), no enzyme (black symbols) and gelatin alone (gray symbols).

As shown by the curves in FIG. 4, the gelatin triple helix formation kinetics are identical whatever the type of gel. After 900 minutes, the triple helix content varies between 25.5 and 27%. The activity of the hyaluronidase, and also the degradation products thereof, do not therefore have any effect on the physical network: the formation of the protein network therefore takes place independently of the remodeling of the soluble phase.

Example 6

Study of the Effect of the Degradation of the Second Polymer on the First Polymer Network Formed by the Third Enzyme In this example, a biomaterial comprising a first polymer network which is a gelatin gel, the second polymer which is hyaluronic acid, a first enzyme which is hyaluronidase, and a third enzyme which is transglutaminase, is produced. The protocol is described in Example 1 C-a). Various concentrations of hyaluronidase were added to a solution of gelatin at 7% and HA at 1%. The gelling of the chemical gel is obtained by adding 1.5 U/ml of transglutaminase at a temperature of 40° C. As for the physical gel, the hyaluronidase concentrations used are 1, 5 and 10 U/ml.

The degradation of the HA has an effect on the value of G' only over the shortest times. This is linked to the fact that, the faster the solution gels, the faster G' increases. However, whether after 900 min or even starting from 150 min, the G's of the various samples are equivalent to that of the gel containing no HA. Whatever the state of degradation of the polysaccharide, it has no influence on the covalently bridged gelatin network.

Figure 5:
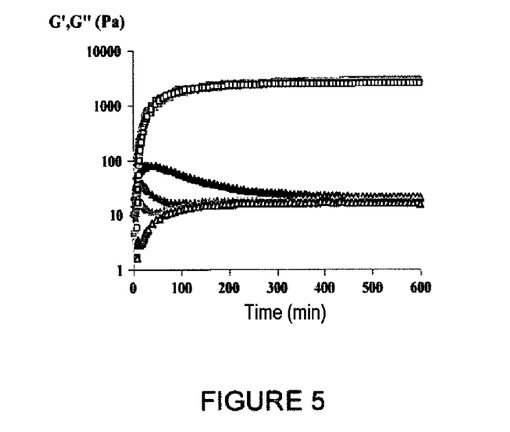
FIG. 5 represents the influence of the degradation of hyaluronic acid (1%) on the viscoelasticity (G': squares, G": triangles) of the chemical gel at a given frequency (6.3 rad·s$^{-1}$) as a function of time in minutes. 1 U/ml of hyaluronidase (black symbols), 5 U/ml of hyaluronidase (dark gray symbols), 10 U/ml of hyaluronidase (light gray symbols) and gelatin alone (white symbols).

On the other hand, depolymerization of the hyaluronic acid has a great deal of influence on the viscosity of the gels. This is because, whatever the amount of enzyme, the G" reaches a maximum before dropping to the value of gelatin (FIG. 5). This example shows that the degradation of a second polymer (HA) included in the aqueous phase of a polymer network (gelatin) induced by a third enzyme (transglutaminase) forming a gel (gel A) does not influence the elasticity (G'), but only the viscosity of the aqueous phase (G").

Example 7

Study of the Effect of the Second Polymer and of the Second Enzyme on the Gel (A) of the Biomaterial According to the Invention The purpose of the example is to demonstrate the effect of the second polymer and of the second enzyme, on the gel (A). In this example, the biomaterial tested comprises:
- as first polymer: gelatin, and therefore as polymer network: a gelatin gel (gel (A)),
- as second polymer: hyaluronic acid,
- as second enzyme: collagenase.

For the preparation of the biomaterial, the samples were prepared with a concentration of 7% gelatin, 1% hyaluronic acid (weight-to-volume ratio) and various final concentrations of collagenase: $0.95 \times 10^{-4}$, $1.12 \times 10^{-4}$, $1.29 \times 10^{-4}$ U/ml. The gelatin powder was incubated with 50 mM Tris-HCl buffer at pH 7.4, and stored at 4° C. for 15 minutes; the hyaluronic acid is then deposited at the surface of the solution. It was then solubilized with stirring at 40° C., at most, for 15 minutes. A collagenase solution, prepared beforehand in the same buffer at an initial concentration at least five times higher than the final concentration, is mixed with the preparation of gelatin and hyaluronic acid.

Figure 6:
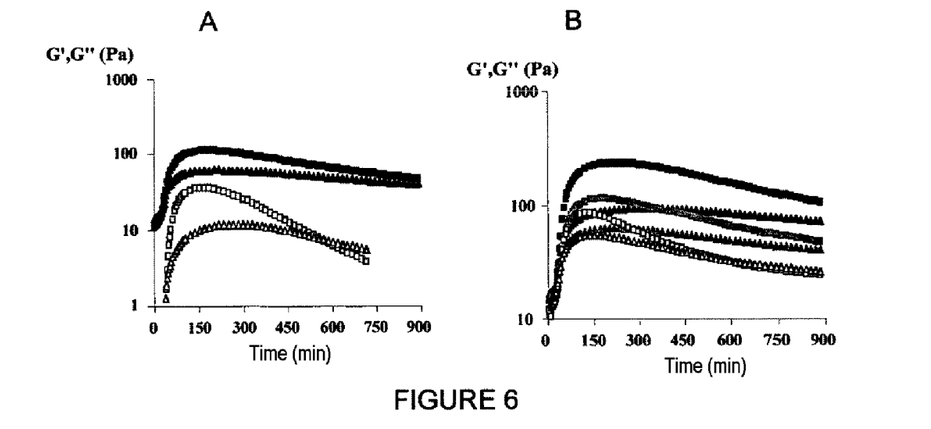

In order to obtain a physical gel, a temperature ramp of 40° C. to 27° C. was applied to the solution, with a decrease in temperature of 0.5° C. per minute. In the presence of hyaluronic acid, the biomaterial gels in 31 minutes (against 40 min without polysaccharide), shows a $G'_{max}$ of 116.5 Pa, and a $G''_{max}$ of 64.4 Pa, and does not exhibit total resolubilization after 900 min (estimated as G'=G"), although the value of G' decreases with time beyond 170 min. Thus, the kinetics and the viscoelasticity of the gels change considerably according to the physiochemical and/or molecular modifications introduced by the polysaccharide (FIG. 6 A). It is possible to obtain total resolubilization of the gel (with, as reference, G'=G" for the gel/sol transition time) using a collagenase concentration of $1.29 \times 10^{-4}$ U/ml (FIG. 6 B). Thus, we have shown that a sol/gel then gel/sol double transition as described in WO 2006/056700 is possible by integrating a second polymer (HA).

Example 8

Study of the Effect of the Second Polymer and of the Second Enzyme on the Gel (A) Formed by the Third Enzyme of the Biomaterial According to the Invention The purpose of the example is to determine whether the sol/gel then gel/sol double transition catalyzed by the action of the second enzyme (collagenase) and third enzyme (transglutaminase) on the first polymer network (gelatin gel) is influenced by the presence of the second polymer (HA). For the preparation of the biomaterial, the samples were prepared with a concentration of 7% gelatin, 1% hyaluronic acid (weight-to-volume ratio), 1.5 U/ml of transglutaminase and various final concentrations of collagenase ($2.06 \times 10^{-4}$, $2.32 \times 10^{-4}$, $2.58 \times 10^{-4}$ U/ml). The gelatin powder was incubated with 50 mM Tris-HCl buffer at pH 7.4, and stored at 4° C. for 15 minutes; the hyaluronic acid is then deposited at the surface of the solution. It was then solubilized with stirring at 40° C., at most, for 15 minutes. A solution of hyaluronidase and transglutaminase, prepared beforehand in the same buffer at an initial concentration at least five times higher than the final concentration, is mixed with the preparation of gelatin and hyaluronic acid.

Figure 7:
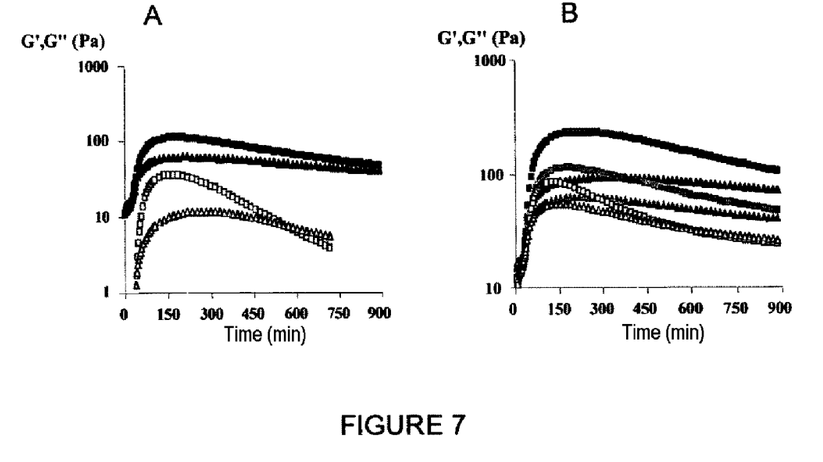

The gelatin/HA system gels in 3.1 min, whereas the "gelatin alone" system gels in 15 min. The maximum viscoelasticity is also greatly increased in the presence of the polysaccharide, since the value of $G'_{max}$ is 264 Pa (50 Pa without HA) and that of $G''_{max}$ is 61.7 Pa (4.4 Pa without HA). Finally, the total resolubilization time of the gel is 396 min against 152 min in the other case (FIG. 7).

The intrinsic viscoelasticity of hyaluronic acid therefore leads the viscoelasticity of the system to increase more rapidly when gelling occurs, so as to give a stronger gel, and, finally, limits its resolubilization by collagenase. Thus, the sol/gel(A)-gel(A)/sol double transition catalyzed by the action of the second and third enzymes on the first polymer network is influenced by the presence of the second polymer.

Example 9

Study of the Effect of the Degradation of the Second Polymer by the First Enzyme Combined with the Action of the Second Enzyme on the Gel (A) of a Biomaterial According to the Invention The purpose of the example is to determine whether the sol/gel-gel/sol double transition catalyzed by the action of the second enzyme (collagenase) on the first polymer network (gelatin gel) is influenced by the degradation of the second polymer (HA) by the first enzyme (hyaluronidase). The biomaterial is prepared according to the protocol of Example B.

Figure 8:
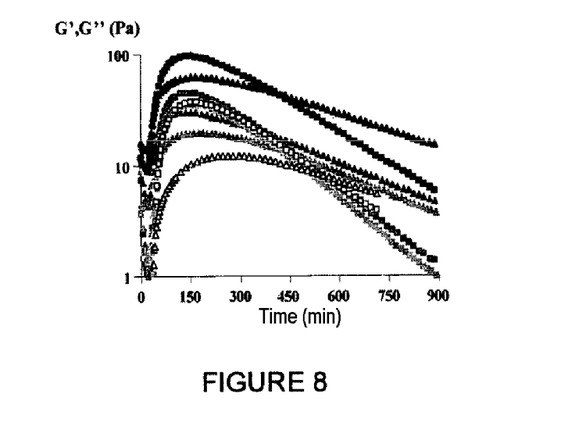
FIG. 8 represents the influence of the degradation of hyaluronic acid (1%) on the viscoelasticity (G': squares, G": triangles) of the physical gel containing collagenase (1.12×10$^{-4}$ U/ml), at a given frequency (6.3 rad·s$^{-1}$) as a function of time. 1 U/ml of hyaluronidase (black symbols), 5 U/ml of hyaluronidase (dark gray symbols), 10 U/ml of hyaluronidase (light gray symbols) and gelatin alone (white symbols).

The change in viscoelasticity is different depending on the amount of Hase used (FIG. 8). Compared with the biomaterial with HA and without Hase, the rheological parameters fall substantially. A synergy becomes established between the collagenase and hyaluronidase activities, and can be observed both in terms of the loss modulus and in terms of the storage modulus.

Thus, the sol/gel(A)-gel(A)/sol double transition catalyzed by the action of the second enzyme (collagenase) on the polymer network (gelatin gel) is influenced by the degradation of the second polymer (HA) by the first enzyme (hyaluronidase). The same conclusions can be put forward when, during the preparation of the biomaterial, the collagenase is replaced with thermolysin or trypsin, as described in Example 1 B.

Example 10

Figure 9:
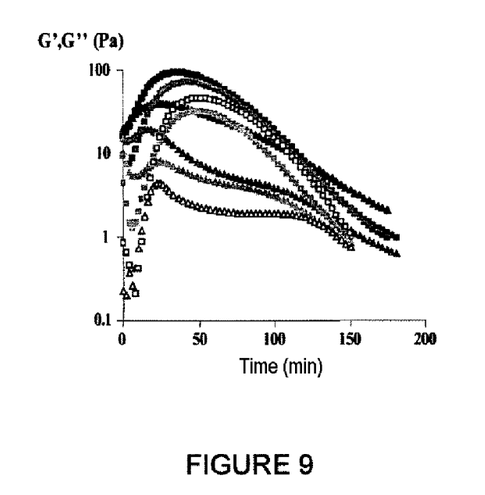
FIG. 9 represents the influence of the degradation of hyaluronic acid (1%) on the viscoelasticity (G': squares, G": triangles) of a chemical gel containing transglutaminase (1.5 U/ml) and collagenase ($2.32 \times 10^{-4}$ U/ml), at a given frequency (6.3 rad·s$^{-1}$) as a function of time. 1 U/ml of hyaluronidase (black symbols), 5 U/ml of hyaluronidase (dark gray symbols), 10 U/ml of hyaluronidase (light gray symbols) and gelatin alone (white symbols).

Study of the Effect of the Degradation of the Second Polymer by the First Enzyme Combined with the Action of the Second Enzyme on the Gel (A) Formed by a Third Enzyme The purpose of the example is to determine whether the sol/gel-gel/sol double transition catalyzed by the action of the second enzyme (collagenase) on the polymer network (gelatin gel) formed by a third enzyme (transglutaminase) is influenced by the degradation of the second polymer (HA) generated by the first enzyme (hyaluronidase). The biomaterial is prepared according to the protocol of Example D. The characteristics of the biomaterial, with HA, depend on the concentration of hyaluronidase used (FIG. 9).

Thus, a synergy appears to become established between the two hydrolases, said synergy resulting in a greater decrease in the viscoelasticity compared with the biomaterial without Hase. Thus, the sol/gel-gel/sol double transition catalyzed by the action of the second enzyme (collagenase) on the polymer network (gelatin gel) formed by a third enzyme (transglutaminase) is influenced by the degradation of the second polymer (HA) generated by the first enzyme (hyaluronidase). The same conclusions can be put forward when, during the preparation of the biomaterial, the collagenase is replaced with thermolysin or trypsin, as described in Example 1 D.

Example 11

Azure Blue Release by the Biomaterial According to the Invention

In this example, azure blue release from a biomaterial was studied. The biomaterial tested comprises:
- as first polymer: gelatin, and therefore as first polymer network: a gelatin gel (gel (A)),
- as second polymer: hyaluronic acid,
- as first enzyme: hyaluronidase,
- as third enzyme: transglutaminase, and
- azure blue.

In the present example, the gelatin is at a concentration of 7% and the transglutaminase at 1 U/ml in the various gels. When it is present, the hyaluronic acid is at a concentration of 1% and the hyaluronidase at 15 U/ml.

A solution of 50 mM Tris-HCl buffer at pH 7.4, containing 1.25 mg/ml of azure blue (Sigma (registered trademark)) is added to gelatin powder. A 1.5% hyaluronic acid solution is then added to the gelatin solution, and the mixture is incubated at 40° C. for 30 min. An enzyme solution (either transglutaminase alone, or transglutaminase and hyaluronidase), prepared in the same buffer, is then mixed into the gelatin solution. The mixture is placed at 40° C.

A gel containing gelatin and transglutaminase (TG) and azure blue was therefore obtained. A gel containing gelatin, hyaluronic acid (HA), transglutaminase (TG) and azure blue was obtained. Finally, a gel containing gelatin, hyaluronic acid (HA), transglutaminase (TG), hyaluronidase and azure blue was obtained.

Figure 10:
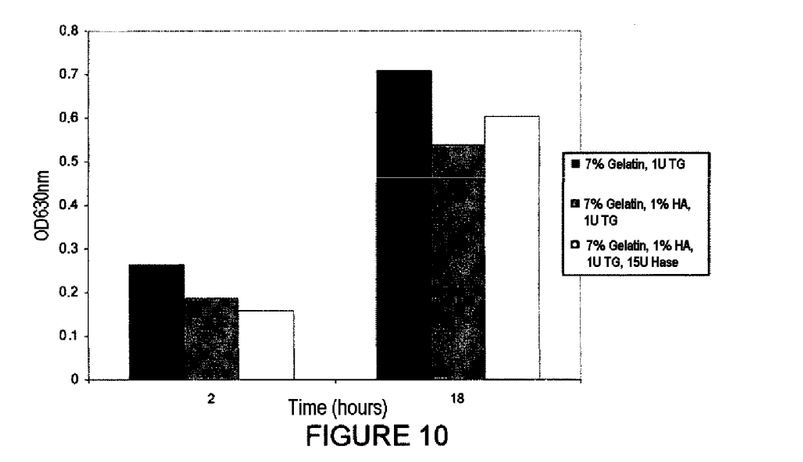
FIG. 10 represents the release, as a function of time, at 40° C., of azure blue from various gelatin (7%) gels obtained with 1 U/ml of transglutaminase. Without hyaluronic acid (black bar), with 1% hyaluronic acid (gray bar), with 1% hyaluronic acid and 15 U/ml of hyaluronidase (white bar).

The release of the azure blue as a function of time and as a function of the gel was measured (FIG. 10) by measuring the optical density (OD at 630 nm) of the medium in which the various gels were contained. The measurement of the azure blue release is as a function of the components of the gel (FIG. 10). This experiment clearly demonstrates that the biomaterial of the invention allows the release of substances, and that this release is controlled.

Example 12

Hyaluronic Acid Release by the Biomaterial According to the Invention

In this example, hyaluronic acid release from a biomaterial was studied. The biomaterial tested comprises:
- as first polymer: gelatin, and therefore as first polymer network: a gelatin gel (gel (A)),
- as second polymer: hyaluronic acid,
- as first enzyme: hyaluronidase.

The biomaterials all contain 3% gelatin and were obtained by incubation at 20° C. When it is present, the hyaluronic acid is at a concentration of 1% and the hyaluronidase at 15 U/ml.

The gel was obtained by means of the following method: a solution of 50 mM Tris-HCl buffer at pH 7.4 was added to gelatin powder. A 1.5% hyaluronic acid solution was then added to the gelatin solution, and then the mixture was incubated at 40° C. for 15 min. For the gel containing hyaluronidase, a solution containing the enzyme, prepared in the same buffer, was then mixed into the gelatin solution, and the mixture was placed at 20° C.

The hyaluronic acid release from the gels was evaluated by polarimetry. The polarimetry used was identical to that of Example 5. This substance release is controlled as a function of size and is controlled over time.

|  | 3% gelatin | 3% gelatin 1% HA | 3% gelatin 1% hyaluronic acid 15 U/ml of hyaluronidase |
|---|---|---|---|
| $\alpha$0 min | −0.7740 | −0.8700 | −0.8866 |
| $\alpha$400 min | −0.7578 | −0.8422 | −0.8264 |
| % hyaluronic acid release | — | 12% | 39% |

The biomaterial of the invention therefore allows controlled release of hyaluronic acid included in a gelatin gel. The release of substance contained in the aqueous phase of a simple gel is modulated by modifying the viscosity of the aqueous phase. The biomaterial of the invention therefore allows a controlled release of substances.

The invention claimed is:
1. A biomaterial comprising an aqueous phase and a first protein polymer network comprising gelatin, in which the first protein polymer network and the aqueous phase form a first gel, the biomaterial further comprising:
- a saccharide polymer comprising hyaluronic acid or alginate, the saccharide polymer being different than the first protein polymer network, and being included in the gel either in solution in the aqueous phase of the gel, or in the form of a second gel; and
- a first enzyme for degrading the saccharide polymer, the first enzyme being hyaluronidase or alginate lyase.

2. The biomaterial as claimed in claim 1, in which the saccharide polymer is hyaluronic acid.

3. The biomaterial as claimed in claim 2, in which the first enzyme is hyaluronidase.

4. The biomaterial as claimed in claim 1, further comprising a second enzyme different than the first enzyme and capable of degrading the first polymer network, the first polymer network being capable of performing, under the action of the second enzyme, a first gel solution transition.

5. The biomaterial as claimed in claim 4, in which the second enzyme is chosen from the group consisting of collagenase, trypsin, and thermolysin.

6. The biomaterial as claimed in claim 5, in which the biomaterial further comprises a third enzyme different than the first and second enzymes and capable of generating bonds between the first polymers or mixture of first polymers, and the third enzyme being capable of catalyzing a solution/gel transition.

7. The biomaterial as claimed in claim 6, in which the third enzyme is transglutaminase.

8. The biomaterial as claimed in claim 1, in which the first protein polymer network is between 0.1% and 20% by weight, relative to the total weight of the biomaterial.

9. The biomaterial as claimed in claim 1, in which the saccharide polymer is between 0.01% and 20% by weight, relative to the total weight of the biomaterial.

10. The biomaterial as claimed in claim 1, in which an active substance is in solution in the aqueous phase and/or in the saccharide polymer.

11. The biomaterial as claimed in claim 10, in which the active substance is chosen from the group consisting of bacteriostatics, bactericides, dyes, including eosin, dextran blue, methylene blue, azure blue, proteins, saccharides, including hyaluronic acid and alginates, a liposome, a nanoparticle, a micelle, anti-acne agents, anti-allergic agents, anxiolytics, anti-asthmatics, anticancer agents, hypolipemic agents, hormonal contraceptives, antidepressants, antidiabetic agents, antalgics, antiasthenics, antihypertensives, antifungals, antibiotics, sleeping drugs, hormone treatments, anti migraine agents, drugs used to treat excess weight, antiparkinsonian agents, neuroleptics, nonsteroidal anti-inflammatories, ovulation inducers, mucolytics, antitussives, erection inducers and antiulceratives.

12. A device for the controlled release of an active substance comprising the biomaterial as defined in claim 1.

13. The device as claimed in claim 12, in which the device is chosen from the group comprising medical devices, including contact lenses, electrodes, sensors, care devices, dressings, impregnated compresses, bandages, surgical dressings, ophthalmic dressings, dental dressings, suture products, therapy devices, orthopedic articles, surgical implants, patches, transdermal gels, active patches, endoprostheses and implants for soft tissues, devices for tissue engineering, reconstruction materials, devices for cell culture, culture media, and culture supports.

14. The biomaterial as claimed in claim 1, wherein the saccharide polymer comprises alginate, and the first enzyme is alginate lyase.

* * * * *